United States Patent [19]

Sajtos

[11] Patent Number: 4,607,126
[45] Date of Patent: Aug. 19, 1986

[54] PROCESS FOR THE PREPARATION OF GLYOXAL, ALKYLGLYOXALS AND ACETALS THEREOF

[75] Inventor: Alexander Sajtos, Linz, Austria

[73] Assignee: Chemie Linz Aktiengesellschaft, Linz, Austria

[21] Appl. No.: 682,019

[22] Filed: Dec. 17, 1984

[30] Foreign Application Priority Data

Dec. 21, 1983 [DE] Fed. Rep. of Germany ....... 3346266

[51] Int. Cl.$^4$ ............................................ C07C 45/53
[52] U.S. Cl. .................................. 568/385; 568/392; 568/567; 568/465
[58] Field of Search ............... 568/469, 385, 567, 392, 568/465

[56] References Cited

U.S. PATENT DOCUMENTS

| | | | |
|---|---|---|---|
| 1,902,070 | 3/1933 | Halbig et al. ....................... | 568/465 |
| 2,288,211 | 6/1942 | Schulz ................................ | 568/465 |
| 2,733,270 | 1/1956 | Fisher ................................. | 568/469 |
| 4,107,217 | 8/1978 | Schreiber et al. .................. | 568/392 |
| 4,434,305 | 2/1984 | Kurosaka et al. .................. | 568/385 |

FOREIGN PATENT DOCUMENTS 2514001 10/1976 Fed. Rep. of Germany ...... 568/469
2513999 10/1976 Fed. Rep. of Germany ...... 568/469

OTHER PUBLICATIONS

Bestmann et al, Chem. Ber., vol. 116, pp. 3264–3266 (1983).
Jung et al, Chem. Abst., vol. 96, #85027a (1982).

*Primary Examiner*—James H. Reamer
*Attorney, Agent, or Firm*—Mark Dryer

[57] ABSTRACT

The invention relates to a process for the preparation of glyoxal, alkylglyoxals and acetals thereof by reacting $\alpha,\beta$-unsaturated dialkylacetals with the equivalent amount of ozone and subsequently subjecting the ozonization products to catalytic hydrogenation, the peroxide-containing ozonization solution being fed continuously into a suspension of the hydrogenation catalyst, while a peroxide content of not more than 0.1 mole/liter is maintained, and cleaving the ozonization products by reduction, after which the dialkylacetals formed in the hydrogenation are, if desired, cleaved to give glyoxal or alkylglyoxals.

11 Claims, No Drawings

PROCESS FOR THE PREPARATION OF GLYOXAL, ALKYLGLYOXALS AND ACETALS THEREOF

The invention relates to a process for the preparation of glyoxal, alkylglyoxals and acetals thereof from $\alpha,\beta$-unsaturated dialkylacetals.

Processes for the preparation of monoacetals of glyoxal from dialkylacetals of $\alpha,\beta$-unsaturated aldehydes by means of an ozonolysis and reduction process have been described occasionally. In Chemische Berichte 36 (1903), page 1935, it is stated that the diethylmonoacetal of glyoxal is formed when ozone acts on acrolein diethylacetal in an aqueous emulsion. No yields are, however, stated in this reference, and the substrate obtained was not characterized in greater detail. The reworking, quoted in German Offenlegungsschrift No. 2,514,001, of the process described in Chem. Berichte Led, however, to a realization that the reaction mixture formed in the course of the ozonization can explode in a shattering manner without a discernible cause. The unsuitability of the known process is made clear in Example 4 of the Offenlegungsschrift, where it is stated that the reaction mixture formed by passing an $O_2/O_3$ mixture into an aqueous solution of acrolein dimethylacetal exploded in a shattering manner with complete destruction of the apparatus.

In order to avoid these difficulties, another process for the preparation of glyoxal monoacetals is therefore suggested in German Offenlegungsschrift No. 2,514,001, in which the starting materials which are reacted with ozone in organic solvents are not acetals of acrolein, but acetals of crotonaldehyde, which are more difficult to obtain and more expensive, and the ozonization products are then cleaved reductively, preferably by catalytic hydrogenation. In carrying out this process, ozone is passed in excess into a solution of the crotonaldehyde acetal until it leaves the reaction mixture once more at a noticeable rate. In order to protect the hydrogenation catalyst against loss of activity, before the ozonization product is cleaved reductively, the excess ozone must be removed once more, in a further operation, by flushing the reaction solution with an inert gas, for example with nitrogen. The hydrogenation is then carried out by adding, per 100 ml, 1 to 3 g of the catalyst, which is preferably a noble metal catalyst, directly to the reaction mixture obtained in the ozonolysis, and passing hydrogen in until saturation is reached. The publication gives no information on the possibility of regenerating or re-using the noble metal catalysts employed, when the hydrogenation is complete.

If acetals of crotonaldehyde are used, the process remains restricted to the preparation of glyoxal monoacetals. Acetals of alkylglyoxals are not accessible, nor are they described in German Offenlegungsschrift No. 2,514,001.

Surprisingly, the disadvantages attached to the known process can be removed, in accordance with the present invention, by a simple and economical process in which a dialkylacetal of acrolein or an alkylacrolein is reacted with a molar equivalent of ozone, with the avoidance of any excess, and the ozonization product, which contains peroxides, is rapidly reduced by catalytic hydrogenation in a dilute solution, at a very low concentration of peroxides.

The present invention relates, accordingly, to a process for preparing acetals of the formula

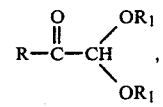   I wherein R represents hydrogen or a linear or branched $C_1$ to $C_6$ alkyl radical and $R_1$ represents a linear or branched $C_1$ to $C_6$ alkyl radical, consisting of (a) dissolving a dialkylacetal of acrolein or of an alphaalkylacrolein of the formula

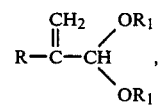   II in which R and $R_1$ have the meaning indicated in formula I, in an organic solvent and reacting said dissolved dialkylacetal of formula II with the equivalent amount of ozone at temperatures from $-80°$ to $0°$ C.;

(b) hydrogenating the peroxide-containing solution thus obtained at a pH-value of 2 to 7 and at temperatures from $15°$ to $45°$ C., said peroxide containing-solution being fed continuously into a suspension of a noble metal catalyst in an organic solvent used in stage (a) at such a rate that a peroxide content of not more than 0.1 mole/liter is set up and maintained in the suspension during the entire course of hydrogenation, while hydrogen is passed in under a pressure of 1 to 3 bar, and then separating the acetals of formula I so formed.

According to a further embodiment of the present invention the resulting acetals of the formula I are cleaved hydrolytically by heating with water in the presence of acids or bases to give the corresponding glyoxal or alkylglyoxals of the general formula

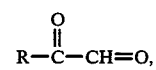   III in which R has the meaning indicated in formula I.

It is preferable to react alkylacrolein dialkylacetals of the formula II in which R and $R_1$ independently of one another represent a linear or branched $C_1$ to $C_4$ alkyl radical. Acetals of the formula II which are reacted particularly preferably are those in which R and $R_1$ independently of one another denote methyl or ethyl, it being in turn very particularly preferable for R and $R_1$ to denote methyl.

The ozonization is preferably carried out at temperatures from $-30°$ to $0°$ C., it being in turn particularly preferable to maintain a temperature from $-15°$ to $-5°$ C. In the process according to the invention, the particular acrolein dialkylacetal used for the reaction is treated with the exactly equivalent amount of ozone, the ozone being reacted quantitatively under the process conditions indicated and stoichiometric amounts of the acetal of the formula II being consumed. As a result of avoiding an excess of ozone, it is possible to prevent the tendency for a spontaneous, explosive decomposition, observed in the ozonization of acetals, nor is it any longer necessary to ensure, after the completion of the ozonization, that excess or unreacted ozone is expelled from the reaction mixture before hydrogenation.

The reaction of the acrolein acetal with ozone in stage (a) is effected in an organic solvent. Suitable organic solvents are unsubstituted or chlorinated hydrocarbons, such as, for example, cyclohexane or petroleum ether, mixtures of hydrocarbons, carbon tetrachloride, chloroform, methylene chloride, ethyl acetate or, advantageously, lower aliphatic alcohols. The preferred solvents, are, above all, methanol or ethanol, the use of methanol being in turn particularly preferred.

In the process according to the invention, the catalytic hydrogenation of the ozonolysis product is carried out in a very dilute solution, and care is taken by means of suitable measures and devices, to ensure that a peroxide content of not more than 0.1 mole/liter, preferably not more than 0.05 mole/liter and especially not more than 0.02 mole/liter, is set up and maintained in the hydrogenation solution during the entire hydrogenation reaction. In order to carry out the reaction in a practical manner, a suspension of the catalyst in the solvent used in the ozonization in stage (a), preferably in a lower aliphatic alcohol, very preferentially in methanol, is initially taken, for example in a hydrogenation reactor, and the solution obtained in the ozonization reaction is fed in continuously by means of a controllable metering device. Care must, of course, be taken in adding the ozonolysis solution at the start and in the course of the hydrogenation, that the peroxide content indicated above is not exceeded in the hydrogenation solution as a result of the amount of peroxide-containing ozonization products added.

As a result of the low concentration of peroxide-containing ozonization products during the actual hydrogenation process, the ratio between the catalyst and the substrate to be reduced is very advantageous, so that, even if the catalyst is used sparingly, rapid reduction is ensured. Poisoning of the catalyst, and the loss in activity associated therewith, which would otherwise be observed at high peroxide concentrations, is also prevented in this way.

Regarded as a whole, however, the continuous feeding-in enables a large amount of ozonization product to be reduced in a relatively small volume, as a result of which concentrated solutions of the acetals of the glyoxal or alkylglyoxal are obtained in the final stage of the process, and not only solvents, but also time and expense are saved in the removal of the solvents by distillation.

Suitable catalysts are the noble metal catalysts customarily used for hydrogenation reactions, and these can be employed in the form of powder catalysts with supporting materials or without a supporting material. It is preferable to use palladium or platinum catalysts, in particular platinum catalysts without a supporting material. In the case of powder catalysts, examples of suitable supporting materials are charcoal, aluminium, silica gel or kieselguhr. The yields in the process according to the invention are, in themselves, independent of the amount of catalysts employed, but, in order to achieve an adequate rate of hydrogenation, it is advisable to take the said catalysts in amounts of noble metal of 0.1 to 5% by weight, preferably of 0.5 to 2% by weight, relative to the particular total amount, fed in per hour, of ozonized acrolein or alkylacrolein dialkylacetal.

When the hydrogenation process is complete, the catalyst is separated off from the reaction mixture and, without regeneration, employed for reductive cleavage in further reaction cycles, no loss in the activity of the catalyst being observed.

The hydrogenation is continued until no further absorption of hydrogen can be detected. In the process according to the invention, equivalent amounts of hydrogen are consumed for the reduction of the ozonization products. The amount of hydrogen which can be used in the hydrogenation ranges from one molar equivalent up to a several times molar excess. The use of excess hydrogen affords no advantages in itself and is only expedient to ensure an adequate supply of hydrogen to the hydrogenation mixture.

In the process according to the invention, the hydrogenation is advantageously carried out under conditions of virtually atmospheric pressure. Conditions of virtually atmospheric pressure are to be understood here as meaning pressures from 1 to about 3 bar, such as are customary in the art, in order to prevent the penetration of air into the hydrogenation reactor. The reduction of the ozonization products can be carried out very simply, from the technical point of view, in this way. It is also possible, however, to carry out the hydrogenation under a pressure of up to 20 bar and thus to increase the rate of hydrogenation.

The reduction takes place with the evolution of heat and, in accordance with a preferred embodiment of the present invention, is carried out at 20° to 40° C., in particular at temperatures within the range from 35° to 40° C.

It is advantageous to maintain a pH from 2 to 5 during the hydrogenation. Since acid by-products are formed in small amounts in the course of the hydrogenation, the metered addition of a base, advantageously dilute sodium hydroxide solution, is necessary in order to maintain the desired pH value.

When the hydrogenation is complete, it is advantageous to remove once more the cations, present in the reaction mixture, of the particular base employed, for example by treating the reaction solution with an acid ion exchanger, before the solvent is distilled off and the acetals of the formula I are isolated. Commercially available ion exchangers in the H form can be used for this purpose, for example polystyrene resins carrying sulfonic acid radicals. Working up is effected by distilling off, advantageously under reduced pressure, solvents, water of reaction and any volatile accompanying products which may be present, and by isolating the acetals of the formula I in a pure state, preferably by rectification with or without the addition of auxiliaries. The acetals are obtained in this manner in the process according to the invention in a purity of over 98% and surprisingly free from by-products.

The acetals obtained in accordance with the invention can be cleaved hydrolytically in a simple manner, for example by heating in water with the addition of catalytic amounts of acids, to give glyoxal or the corresponding alkylglyoxal of the formula III.

It is particularly advantageous to carry out the hydrolytic cleavage of the acetals in the presence of a strongly acid ion exchanger as catalyst, since by means of this method the catalyst can be removed once more from the reaction mixture in a simple manner when the hydrolysis is complete. However, it is not necessary here to isolate the acetals after the hydrogenation; the hydrolysis can be carried out without further treatment in the hydrogenation solution when hydrogenation is complete and the catalyst has been removed.

The $\alpha,\beta$-unsaturated acetals of the formula II which are required as starting substances can be prepared in a known manner, for example by acetalizing $\alpha,\beta$- unsaturated aldehydes by adding dehydrating agents in accordance with the process described in Org. Synth. IV, pages 21-22, or by chlorinating saturated aldehydes, acetalizing the products and eliminating HCl, which is described in Chemisches Zentralblatt 1937 I, pages 5098 et seq.

The process products of the formula I are valuable starting materials and intermediate products from which it is possible to prepare, for example, substances having a considerable biological and pharmacological importance.

The process according to the invention is illustrated in greater detail in the following examples.

EXAMPLE 1

Glyoxal dimethylacetal 918 g (9 moles) of acrolein dimethylacetal, dissolved in 6 liters of methanol, are reacted with the equivalent amount of ozone at $-15°$ to $-10°$ C. by passing in a stream of 1,000 liters/hour of oxygen containing 4% by weight (=1.17 moles/hour) of ozone. Ozone is absorbed quantitatively in this reaction, and the residual content of acrolein dimethylacetal, after the completion of the ozonization, is less than 1% of the initial concentration.

The solution obtained in the ozonization reaction is divided into portions and is continuously fed, via a metering vessel, to a hydrogenation reactor in which is placed a suspension, in 1 liter of methanol, of 5 g of platinum, prepared by reducing $PtO_2$ with $H_2$ in situ, and which is filled with hydrogen, at such a rate that the peroxide content in the hydrogenation solution at the start of and in the course of the entire hydrogenation is not more than 0.02 mole/liter. Hydrogenation is carried out with vigorous stirring and addition of hydrogen until a sample gives a negative peroxide test, the temperature being kept at 35° to 40° C. by external cooling. The hydrogen consumed in replenished continuously from a stock vessel, and a pH of 2 to 4 is maintained in the solution by adding methanolic NaOH. A total of 159 standard liters of $H_2$ (79% of theory) are absorbed during the hydrogenation.

Working up is effected by filtering the contents of the hydrogenation reactor, except for a residue of 1 liter, with suction through a frit. The solution filtered with suction from the hydrogenation reactor is treated with an acid ion exchanger (Lewatit) and the solvent and also volatile accompanying products are distilled off under reduced pressure. The residue containing the reaction product is purified by rectification, and 758 g (7.29 moles) of glyoxal dimethylacetal are obtained, corresponding to a yield of 81% of theory.

The catalyst remaining in the hydrogenation reactor in the smaller portion of the hydrogenation solution is re-used, without regeneration or working up, for the reductive cleavage reaction, by again feeding ozonized solution of acrolein dimethylacetal into the reactor via the metering vessel, and by repeating the hydrogenation process under the reaction conditions indicated above.

EXAMPLE 2

Methylglyoxal dimethylacetal 1,044 g (9 moles) of methacrolein dimethylacetal, dissolved in 6 liters of methanol are initially placed in a reactor and are reacted with ozone as indicated in Example 1 by passing in an $O_2/O_3$ mixture (1,000 liters/hour of $O_2$ and 56 g/hour of $O_3$) at temperatures from $-10°$ to $-5°$ C. Ozone is absorbed quantitatively in this reaction and a stoichiometric amount of methacrolein dimethylacetal is consumed. The residual content of methacrolein dimethylacetal after the completion of the ozonization is less than 0.8% of the initial concentration.

A suspension of 4 g of Pt in 1 liter of methanol is initially placed in a hydrogenation reactor, and, while the mixture is stirred and hydrogen is passed in, the solution obtained in the ozonization reaction is fed in in such amounts that the peroxide content in the hydrogenation reactor does not exceed 0.05 mole/liter at the beginning of and in the course of the hydrogenation. The reaction mixture is kept at a temperature of 25° to 30° C. by external cooling, and the pH is adjusted to a value of 4-5 by metered addition of methanolic NaOH via an automatic pH control mechanism. The reaction mixture becomes free from peroxide 5 to 10 minutes after the completion of the addition of the ozonization solution. The absorption of $H_2$ is 180N l (89.3% of theory).

Working up is effected by filtering the contents of the hydrogenation reactor with suction through a frit and freeing the reaction solution from sodium by means of an acid ion exchanger (Lewatit). Methanol and the volatile accompanying products formed in the reductive cleavage are distilled off on a thin film evaporator, and the residue containing the reaction product is neutralized with sodium hydroxide. The water originating from the hydrogenation is then removed from the system azeotropically by means of petroleum ether, and the residue containing the reaction product is rectified after the addition of urea.

956 g (8.1 moles) of methylglyoxal dimethylacetal are obtained, corresponding to a yield of 90% of theory and boiling at 76° C./100.

EXAMPLE 3

The ozonolysis and reduction process described in Example 2 is repeated, using methacrolein dimethylacetal, and the contents of the hydrogenation reaction are filtered with suction, after the completion of the hydrogenation, until 1 liter of the solution and catalyst remains in the hydrogenation reactor. A new batch of ozonization product is metered into this residue under the conditions indicated above and cleavage by reduction is carried out by passing in hydrogen. In a total of 10 successive reduction cycles, the consumption of hydrogen in each reaction cycle remains approximately the same as in the first batch, the total consumption being 1,774 standard liters (79.2 moles of $H_2$, 88% of theory). The total yield of methylglyoxal dimethylacetal is 9,511 g (80.5 moles), corresponding to 89.4% of theory.

EXAMPLE 4

Methylglyoxal diethylacetal 1 liter of an ethanolic solution of 216 g (1.5 moles) of methacrolein diethylacetal is reacted with ozone analogously to the procedure indicated in Example 1, and is then hydrogenated. Absorption of $H_2$ is 30 standard liters (89.3% of theory).

After working up, which is carried out analogously to the instructions in Example 2 by treating the reaction mixture with an acid ion exchanger, distilling off the solvent and rectifying the reaction product, 189 g of pure methylglyoxal diethylacetal boiling at 69° C./25 are obtained, corresponding to a yield of 86.3% of theory.

EXAMPLE 5

Methylglyoxal di-n-butylacetal 1 liter of a solution of 300 g (1.5 moles) of methacrolein di-n-butylacetal in ethanol is reacted with ozone analogously to the procedure indicated in Example 1, and is then hydrogenated. The absorption of $H_2$ is 28.5 standard liters (84.8% of theory).

After working up, which is carried out analogously to the instruction in Example 2 by treating the reaction solution with an acid ion exchanger (Lewatit), distilling off the solvent and rectifying the reaction product, 245 g of pure methylglyoxal di-n-butylacetal boiling at 104° C./15 are obtained, corresponding to a yield of 81% of theory.

EXAMPLE 6

Ethylglyoxal dimethylacetal 1 liter of a solution of 195 g (1.5 moles) of ethylacrolein dimethylacetal in methanol is reacted with ozone at $-25°$ C. to $-30°$ C. analogously to the procedure indicated in Example 1, and is then hydrogenated. The absorption of $H_2$ is 29.55 standard liters (87.8% of theory). After working up, which is carried out analogously to the instructions in Example 2 by removing the catalyst, treating the reaction solution with an acid ion exchanger, distilling off the solvent and rectifying the reaction product, 169 g of ethylglyoxal dimethylacetal boiling at 52° C./15 are obtained, corresponding to a yield of 85.4% of theory.

EXAMPLE 7 n-Butylglyoxal dimethylacetal 1 liter of a solution of 237 g (1.5 moles) of n-butylacrolein dimethylacetal in methanol is reacted with ozone analogously to the procedure indicated in Example 1 and is then hydrogenated. The absorption of $H_2$ is 29 standard liters.

After working up, which is carried out analogously to the instructions in Example 2 by removing the catalyst, treating the reaction solution with an acid ion exchanger, distilling off the solvent and rectifying the reaction product, 199 g of n-butylglyoxal dimethylacetal boiling at 80° C./12 are obtained, corresponding to a yield of 82.9% of theory.

EXAMPLE 8

Methylglyoxal dimethylacetal.

1 liter of a solution of 174 g (1.5 moles) of methacrolein dimethylacetal in ethyl acetate is reacted with the equivalent amount of ozone at $-45°$ to $-50°$ C. analogously to the procedure indicated in Example 1. Hydrogenation is carried out by initially placing a suspension in ethyl acetate of 5 g of a catalyst containing 10% of Pd on active charcoal in a hydrogenation reactor filled with hydrogen, and feeding in the solution obtained in the ozonization reaction via a metering vessel at such a rate that the peroxide content in the hydrogenation solution at the start and in the course of the entire hydrogenation is not more than 0.1 mole/liter, and continuing hydrogenation at 25° to 30° C. and at a pH value of 3 to 4 until a sample gives a negative peroxide test.

After working up, which is carried out analogously to the instructions in Example 2 by removing the catalyst, treating the reaction solution with an acid ion exchanger, distilling off the solvent and rectifying the reaction product, 108 g of methylglyoxal dimethylacetal boiling at 76° C./100 are obtained, corresponding to a yield of 61% of theory.

EXAMPLE 9

Isobutylglyoxal diethylacetal 1. liter of a solution of 242 g (1.3 moles) of isobutylacrolein diethylacetal in ethanol is reacted with ozone analogously to the procedure indicated in Example 1 and is then hydrogenated while a pH value of 4 to 5 is maintained. The absorption of $H_2$ is 25.5 standard liters (87.5% of theory).

After working up, which is carried out analogously to the instructions in Example 2, 205 g of pure isobutylglyoxal diethylacetal boiling at 88° C./25 are obtained, corresponding to a yield of 84% of theory.

EXAMPLE 10

Hydrolytic cleavage of methylglyoxal dimethylacetal to give methylglyoxal 118 g (1 mole) of methylglyoxal dimethylacetal and 250 g of water are heated with 5 g of a strongly acid ion exchanger (Lewatit in the $H^+$ form), and the methanol/water mixture is distilled off. This gives 198 g of an aqueous solution of methylglyoxal containing 35.9% by weight: Methylglyoxal dimethylacetal is thus cleaved hydrolytically to give a quantitative yield of methylglyoxal.

What we claim is:

1. Process for preparing acetals of the formula

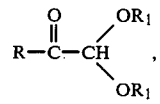

wherein R represents hydrogen or a linear or branched $C_1$ to $C_6$ alkyl radical and $R_1$ represents a linear or branched $C_1$ to $C_6$ alkyl radical, consisting of (a) dissolving a dialkylacetal of acrolein or of an alpha-alkylacrolein of the formula

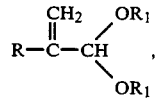

in which R and $R_1$ have the meaning indicated in formula I, in an organic solvent and reacting said dissolved dialkylacetal of formula II with the exact stoichiometric equivalent amount of ozone at temperatures from $-80°$ to $0°$ C.;

(b) hydrogenating the peroxide-containing solution thus obtained at a pH-value of 2 to 7 and at temperatures from 15° to 45° C., said peroxide containing-solution being fed continuously into a suspension of a noble metal catalyst in an organic solvent used in a stage (a) at such a rate that a peroxide content of not more than 0.1 mole/liter is set up and maintained in the suspension during the entire course of hydrogenation while hydrogen is passed in under a pressure of 1 to 3 bar, and then separating the acetals of formula I so formed.

2. The process according to claim 1 in which the ozonization in stage (a) is carried out at temperatures within the range from −15° to −5° C.

3. The process according to claim 1 in which a lower aliphatic alcohol is used as the solvent in the ozonization in stage (a) and in the hydrogenation of the peroxide containing solution in stage (b).

4. The process according to claim 3 in which methanol is used as the solvent in the ozonization in stage (a) and in the hydrogenation of the peroxide containing solution in stage (b).

5. The process according to claim 1 in which the peroxide content of the suspension in stage (b) is not more than 0.02 mole/liter during the entire course of hydrogenation in stage (b).

6. The process according to claim 1 in which platinum without a support is used as the catalyst for the hydrogenation in stage (b).

7. The process according to claim 1 in which the hydrogenation in stage (b) is carried out within the temperature range from 35° to 40° C.

8. The process according to claim 1 in which the pH is adjusted to a value of 2 to 5 during the entire course of hydrogenation in stage (b).

9. The process according to claim 1 in which acetals of the formula II in which R and $R_1$ denote methyl are employed for the reaction.

10. Process for preparing glyoxal or alkylglyoxals of the formula

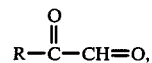

wherein R represents hydrogen or a linear or branched $C_1$ to $C_6$ alkyl radical, consisting of (a) dissolving a dialkylacetal of acrolein or of an alpha-alkylacrolein of the general formula

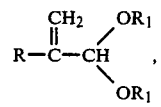

in which R has the meaning indicated in formula III and $R_1$ represents in a linear or branched $C_1$ to $C_6$ alkyl radical, in an organic solvent and reacting said dissolved dialkylacetal of formula II with the exact stoichiometric equivalent amount of ozone at temperatures from −80° to 0° C.

(b) hydrogenating the peroxide-containing solution thus obtained at a pH-value of 2 to 7 and at temperatures from 15° to 45° C., said peroxide containing-solution being fed continuously into a suspension of a noble metal catalyst in an organic solvent used in stage (a) at such a rate that a peroxide content of not more than 0.1 mole/liter is set up and maintained in the suspension during the entire course of hydrogenation while hydrogen is passed in under a pressure of 1 to 3 bar, and then (c) cleaving hydrolytically the resulting acetals of formula I by heating with water in the presence of acids or bases.

11. The process according to claim 10 in which the acetals are cleaved by heating with water in the presence of a strongly acid ion exchanger.

* * * * *